US00PP18918P2

(12) United States Plant Patent
Meilland

(10) Patent No.: US PP18,918 P2
(45) Date of Patent: Jun. 10, 2008

(54) HYBRID TEA ROSE PLANT NAMED 'MEIFACUL'

(50) Latin Name: *Rosa hybrida*
Varietal Denomination: Meifacul

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 34 days.

(21) Appl. No.: 11/636,513

(22) Filed: Dec. 11, 2006

(51) Int. Cl.
*A01H 5/00* (2006.01)

(52) U.S. Cl. ..... Plt./134

(58) Field of Classification Search ..... Plt./134
See application file for complete search history.

*Primary Examiner*—Annette H Para
(74) *Attorney, Agent, or Firm*—Buchanan Ingersoll & Rooney PC

(57) ABSTRACT

A new and distinct variety of Hybrid Tea rose plant is provided that abundantly forms attractive large double blossoms that are yellow in coloration having a pleasant fragrance. An upright growth habit is displayed and the foliage is very dense glossy dark green. The disease tolerance is good particularly with respect to Marsonia. The plant is well suited for providing attractive ornamentation in parks and gardens.

1 Drawing Sheet

Figures 1, 2, 3, 4, 5, 6, 7, 8, 9, 10, 11, 12, 13, 14, 15:
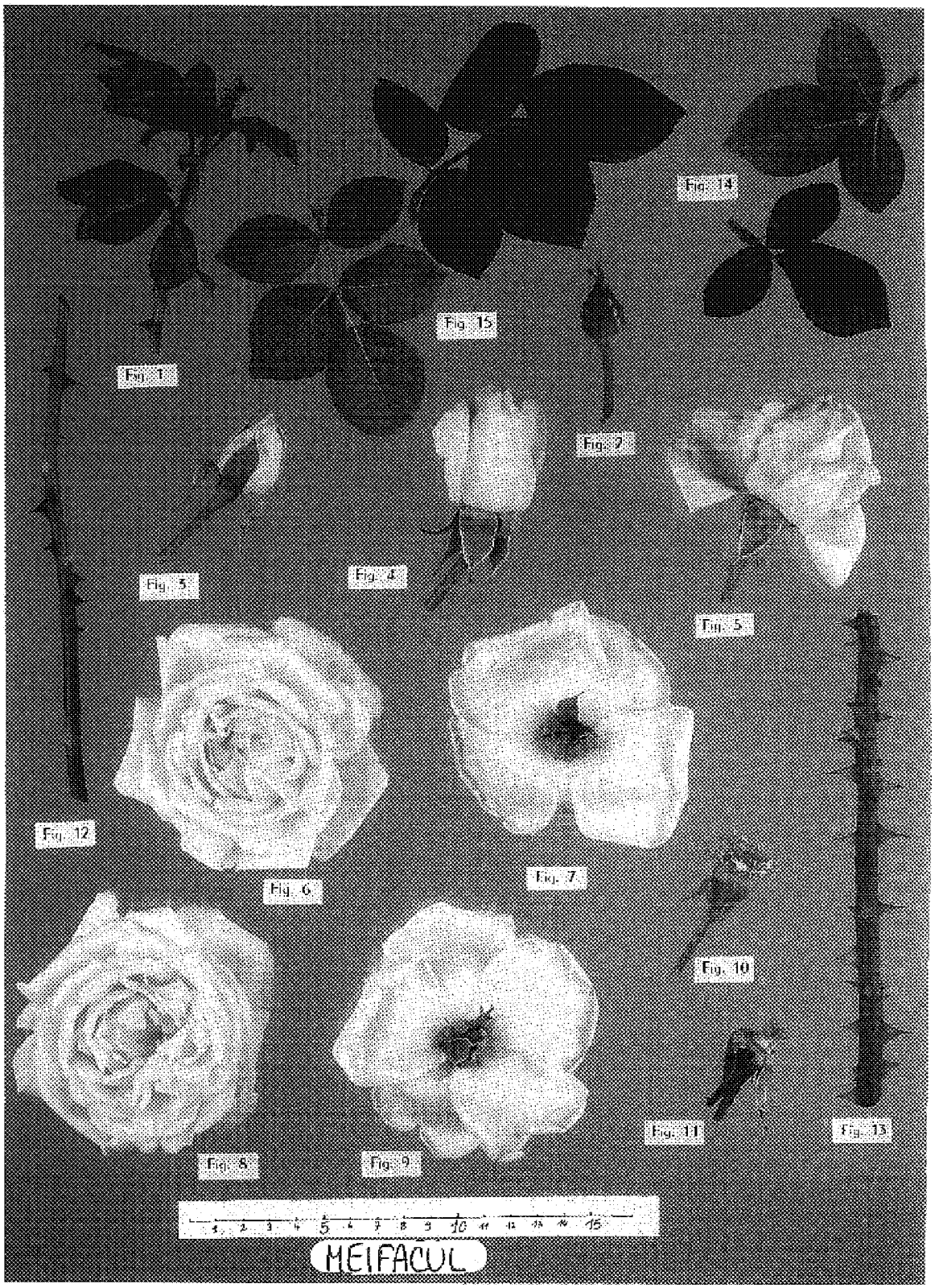

Botanical/commercial classification: *Rosa hybrida*/Hybrid Tea Rose Plant.
Varietal denomination: cv. Meifacul.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) was the product of the cross of the 'Landora' variety (non-patented in the United States) and the 'Meirestif' variety (non-patented in the United States). The 'Landora' variety sometimes is known as the 'Sunblest' variety. The male parent (i.e., the pollen parent) was the product of the cross of the 'Poumidor' variety (non-patented in the United States) and the 'Meicapinal' variety (non-patented in the United States).

('Landora'×'Meirestif')×('Poumidor'×'Meicapinal').

The seeds resulting from the above pollination were sown and small plants were obtained which were physically and biologically different from each other. Selective study resulted in the identification of a single plant of the new variety.

It was found that the new Hybrid Tea rose plant of the present invention:

(a) exhibits an erect growth habit, (b) forms in abundance attractive large double blossoms that are yellow in coloration having a pleasant fragrance, (c) displays very dense glossy dark green foliage, (d) exhibits excellent tolerance to diseases particularly with respect to Marsonia, and (e) is particularly well suited for growing as attractive ornamentation in the landscape.

The new variety well meets the needs of the horticultural industry and can be grown to advantage as attractive ornamentation in parks and gardens.

The new variety can be readily distinguished from its ancestors. For instance, the blossom coloration is considerably different from that of the 'Meirestif,' 'Poumidor' and 'Meicapinal' varieties. More specifically, the 'Meirestif' variety forms bicolored orange-yellow blossoms, the 'Poumidor' variety forms more orange blossoms, and 'Meicapinal' variety forms pink blossoms. The blossoms of the 'Landora' variety are smaller in size than those of the new variety.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another.

The new variety has been named 'Meifacul'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately two year of age and were observed during October while growing on *Rose froebelli* understock outdoors at Le Cannet des Maures, Var, France. Dimensions in centimeters are indicated at the bottom of the photograph.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening;

FIG. 6 — illustrates a specimen of an open flower — plan view — observe;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates specimens of a pair of leaves with three leaflets — plan view — under surface (top) and plan view — upper surface (bottom); and FIG. 15 — illustrates specimens of a pair of leaves with five leaflets — plan view — upper surface (upper-right), and plan-view under surface (lower-right).

DETAILED DESCRIPTION

The chart used in the identification of the colors is that of The Royal Horticultural Society (R.H.S. Colour Chart). The description is based on the observation of two-year-old plants during October while growing budded on *Rosa froebelli* understock and growing outdoors at Le Cannet des Maures, Var, France.

Class: Hybrid Tea.

Plant:

*Height.*—Approximately 140 to 160 cm on average at the end of the growing season.

*Width.*—Approximately 70 to 80 cm on average at the end of the growing season.

*Habit.*—Erect.

Branches:

*Color.*—Young stems: near Yellow-Green Group 146B. Adult wood: near Yellow-Green Group 147C.

*Thorns.*—On young stems: Small prickles: Quantity: none. Long prickles: Configuration: rather upright and elongated, slightly concave on the under surface, and oboval on the base. Quantity: Approximately 9 on average on a stem length of 10 cm. Length: approximately 0.8 cm on average. Color: near Greyed-Orange Group 166A. On adult stems: Small prickles: Quantity: none. Long prickles: Configuration: rather upright and elongated, slightly, concave on the under surface, and oboval on the base. Quantity: approximately 15 on average on a stem length of 10 cm. Length: approximately 0.8 mm on average. Color: near Greyed-Orange Group 166C.

Leaves:

*Stipules.*—Adanate, pectinate and narrow.

*Petioles.*—Upper surface: near Yellow-Green Group 147C in coloration. Under surface: near Yellow-Green Group 146D in coloration. Texture: non-glandular on the upper surface, and with a very few prickles on the under surface. Length: approximately 3.5 cm for the terminal leaflet.

*Rachis.*—Upper surface: near Yellow-Green Group 147C in coloration. Under surface: near Yellow-Green Group 146D in coloration. Texture: smooth.

*Leaflets.*—Number: 3, and 5 (most often). Shape: generally elliptical with a cuneiform tip and a rounded base. Size: the terminal leaflets commonly are approximately 7 cm in length and approximately 4.5 cm in width on average. Serration: small and single (as illustrated). Texture: physically firm and thick. General appearance: very dense with a glossy aspect. Color (young foliage): Upper surface: near Green Group 139A. Under surface: near Green Group 137C. Color (adult foliage): Upper surface: near Green Group 131A. Under surface: near Green Group 137C.

Inflorescence:

*Number of flowers.*—Commonly one to three blossoms per stem.

*Peduncle.*—Smooth, approximately 7 cm in length on average, approximately 0.4 cm in diameter on average, and near Yellow-Green Group 146C suffused with Greyed-Orange Group 166C in coloration.

*Sepals.*—Upper surface: tomentose and near Yellow-Green Group 146C in coloration. Under surface: smooth and near Yellow-Green Group 146A in coloration. Size: near 3 cm in length on average, and near 1.2 cm in width at the widest point on average.

*Buds.*—Shape: conical. Size: large. Length: approximately 3 cm on average. Width: near 2 cm on average at the widest point. Color: Upper surface: near Yellow Group 7B margined with near Yellow Group 7C to 7D. Under surface: near Yellow Group 8B and 8C.

*Flower.*—Shape: cup-shaped. Diameter: approximately 11 to 13 cm on average. Color (in the course of opening): Upper surface: near Yellow Group 7B margined with Yellow Group 7C and 7D. Under surface: near Yellow Group 8B and 8C. Color (when fully open): Upper surface: Yellow Group 7B margined with Yellow Group 7C and 7D. Under surface: near Yellow Group 8B and 8C. Color stability: very slight change with age. Fragrance: pleasant and similar to that of Palmarosa (Rose Geranium). Lasting quality: the blossoms commonly last approximately 10 days on the plant on average, and approximately 8 days on average when cut and placed in a vase. Petal number: approximately 38 to 40 on average under normal growing conditions. Petal shape: with a substantially rounded tip. Petal texture: consistent and somewhat firm. Petal length: approximately 6 cm on average. Petal width: approximately 7 cm on average. Petal arrangement: imbricated; and without petaloids. Petal drop: good with the petals commonly detaching cleanly before drying. Stamen number: approximately 110 on average. Anthers: regularly arranged around the styles, approximately 0.2 cm in size on average, and near Yellow-Orange Group 15A in coloration. Pollen: present and near Yellow-Orange Group 15A in coloration. Filaments: approximately 0.5 cm in length on average and near Red Group 45A in coloration. Pistils: approximately 90 on average. Stigmas: approximately 0.1 cm in size on average and near Orange Group 24B in coloration. Styles: approximately 0.6 cm in length on average, and near Red Group 45A in coloration. Receptacle: smooth, pitcher-shaped in longitudinal section, approximately 1.2 cm in length on average, approximately 1.2 cm in width on average at the widest point, and near Yellow-Green Group 146C in coloration. Hips: generally spherical in shape, approximately 3 cm in length on average, approximately 2.5 cm in width on average, and near Yellow-Green Group 147D suffused with near Orange Group 28B in coloration.

Development:

*Vegetation.*—Very strong.

*Blooming.*—Early, abundant, and recurrent.

*Tolerance to diseases.*—Excellent, particularly with respect to Marsonia.

*Aptitude to bear fruit.*—Few to medium in number.

I claim:

1. A new and distinct Hybrid Tea rose plant characterized by the following characteristics:

(a) exhibits an erect growth habit, (b) forms in abundance attractive large double blossoms that are yellow in coloration having a pleasant fragrance, (c) displays very dense glossy dark green foliage, (d) exhibits excellent tolerance to diseases particularly with respect to Marsonia, and (e) is particularly well suited for growing as attractive ornamentation in the landscape;

substantially as herein shown and described.

* * * * *

MEIFACUL